US011247206B2

(12) United States Patent
Paranjape (10) Patent No.: US 11,247,206 B2
(45) Date of Patent: Feb. 15, 2022

(54) HARVESTING CELL-FREE NON-CODING RNAS (CFNCRS) FROM INTERSTITIAL FLUID FOR SENSITIVE BIOMARKERS

(71) Applicant: Georgetown University, Washington, DC (US)

(72) Inventor: Makarand Paranjape, Silver Spring, MD (US)

(73) Assignee: Georgetown University, Washington, DC (US)

( * ) Notice: Subject to any disclaimer, the term of this patent is extended or adjusted under 35 U.S.C. 154(b) by 232 days.

(21) Appl. No.: 16/475,589

(22) PCT Filed: Jan. 31, 2018

(86) PCT No.: PCT/US2018/016083
§ 371 (c)(1),
(2) Date: Jul. 2, 2019

(87) PCT Pub. No.: WO2018/144506
PCT Pub. Date: Aug. 9, 2018

(65) Prior Publication Data
US 2020/0030796 A1  Jan. 30, 2020

Related U.S. Application Data

(60) Provisional application No. 62/452,820, filed on Jan. 31, 2017.

(51) Int. Cl.
*B01L 3/00* (2006.01)
*A61B 10/00* (2006.01)
(Continued)

(52) U.S. Cl.
CPC .... *B01L 3/502715* (2013.01); *A61B 10/0045* (2013.01); *C12Q 1/6806* (2013.01);
(Continued)

(58) Field of Classification Search
CPC .. B01L 3/502715; B01L 3/5027; B01L 3/502; B01L 3/50; A61B 10/0045;
(Continued)

(56) References Cited

U.S. PATENT DOCUMENTS 5,200,477 A   4/1993   Baker et al. .................... 526/74
6,887,202 B2   5/2005   Currie et al. ................. 600/309
(Continued)

FOREIGN PATENT DOCUMENTS

WO    WO 2017/177131    10/2017    ............. B82Y 30/00

OTHER PUBLICATIONS

J. A. Loo, et al., "Comparative Human Salivary and Plasma Proteomes," J. Dent. Res. 89(10), 1016-1023, 2010.
(Continued)

*Primary Examiner* — Christine T Mui
(74) *Attorney, Agent, or Firm* — Dawn-Marie Bey; Bey & Cotropia PLLC (57) ABSTRACT

A system for determining the presence of cell-free non-coding RNA (cfNCR) biomarkers in interstitial fluid includes a microfluidic device for non-invasively and passively accessing interstitial fluid from a patient. The microfluidic device is formed of a substrate containing multiple vertical micro channels therethrough, wherein at a first end of each of the multiple vertical micro channels a microheater is formed for controllably ablating a portion of dry dead skin cells to access the interstitial fluid; and wherein at a second end of each of the multiple vertical micro channels is a horizontal micro channel for receiving accessed interstitial fluid from a vertical micro channel and guiding the accessed interstitial fluid to a common collection port.

19 Claims, 12 Drawing Sheets

(51) Int. Cl.
  *C12Q 1/6806* (2018.01)
  *C12Q 1/68* (2018.01)
(52) U.S. Cl.
  CPC ... *A61B 2010/008* (2013.01); *A61B 2010/009* (2013.01); *B01L 2300/12* (2013.01); *B01L 2300/165* (2013.01); *B01L 2300/1805* (2013.01); *B01L 2400/0677* (2013.01)
(58) Field of Classification Search
  CPC .............. A61B 10/00; A61B 2010/008; A61B 2010/009; C12Q 1/6806; C12Q 1/68
  USPC ........................................... 422/502, 500, 50
  See application file for complete search history.

(56) References Cited

U.S. PATENT DOCUMENTS

| | | | |
|---|---|---|---|
| 7,931,592 | B2 | 4/2011 | Currie et al. ................. 600/309 |
| 8,568,315 | B2 | 10/2013 | Currie et al. ................. 600/309 |
| 9,332,937 | B2 | 5/2016 | Currie et al. .... A61B 5/150007 |
| 10,004,434 | B1 | 6/2018 | Paranjape .......... A61B 5/14532 |
| 2002/0010412 | A1 | 1/2002 | Eppstein ......................... 604/10 |
| 2002/0187503 | A1 | 12/2002 | Harrold et al. ................... 435/6 |
| 2004/0099310 | A1 | 5/2004 | Andersson .................... 137/240 |
| 2008/0121045 | A1 | 5/2008 | Cole et al. ................. 73/861.08 |
| 2010/0303687 | A1 | 12/2010 | Blaga et al. .................. 422/504 |
| 2011/0178380 | A1 | 7/2011 | Chowdhury .................. 600/345 |
| 2012/0156112 | A1* | 6/2012 | Sprague ............... B01L 3/5025 422/430 |
| 2013/0123595 | A1 | 5/2013 | Currie et al. ................. 600/347 |
| 2013/0289374 | A1 | 10/2013 | Paranjape et al. ............ 600/347 |
| 2014/0025000 | A1 | 1/2014 | Currie et al. .................... 604/66 |
| 2014/0186827 | A1 | 7/2014 | Pieprzyk et al. ............ 435/6.11 |
| 2017/0035331 | A1 | 2/2017 | Paranjape et al. . A61B 5/14514 |

OTHER PUBLICATIONS

J. Kool, et al., "Suction Blister Fluid as a Potential Body Fluid for Biomarker Proteins," Proteomics, 7(20), 3638-3650, 2007.
M. Brunner, et al., "Direct Assesment of Peripheral Pharmokinetics in Humans: Comparison Between Cantharides Blister Fluid Sampling, in vivo Microdialysis and Saliva Sampling," Br. J. Clin. Pharmacol., 46(5), 425-431, 1998.
A.V. Romanyuk,m et al., "Collection of Analytes from Microneedle Patches," Anal. Chem. 86(21): 10520-10523, Nov. 4, 2014.
L. Ebah, "Extraction and Analysis of Interstitial Fluid, and Characterization of the Interstitial Compartment in Kidney Disease," PhD Thesis, University of Manchester, 2012.
Hotovy, et al., "Gallium Arsenide Suspended Microheater for MEMS Sensor Arrays," Microsyst. Technol. 14:629-635, 2008.
Sidek, et al., "Effect of Heater Geometry on the High Temperature Distribution on a MEMS Micro-Hotplate," $3^{rd}$ Asia Symposium on Quality Electronic Design, IEEE, 2011.
Chau, et al., "Design and Fabrication of a Quasi-Ordered Nanoporous Silicon Membrane Suitable for Thermally Induced Drug Release," J. Micromech. Microeng. 22, 085028, 14 pp., 2012.
International Search Report and Written Opinion for PCT Application No. PCT/US17/57614, dated Jan. 4, 2018, 10 pp.
U.S. Appl. No. 13/835,696, Application as filed Mar. 15, 2013 (31 pp.) (Abandoned).
Turchinovich, et al., "The Origin, Function and Diagnostic Potential of Extracellular MicroRNA in Human Body Fluids," Frontiers in Genetics, vol. 5, Article 30, Feb. 2014.
Mielczarek, et al., "Microfluidic Blood Plasma Separation for Medical Diagnostics: Is It Worth It?," DOI: 10.1039/C6LC00833J, (Frontier) Lab Chip, 16, 3441-3448, 2016.
International Search Report and Written Opinion for PCT Application No. PCT/US18/16083, dated May 8, 2018, 15 pp.
Gu, Z., "Experimental and Theoretical Study of Droplet Formation at a T-Junction With Xanthan Gum Solutions," Thesis [online], University of New South Wales, Mar. 2013 [retrieved on Mar. 16, 2018], Retrieved from the Internet: https://core.ac.uk.download/pdf/108115244.pdf, 100 pp.
Madadi, H., "Analysis and Design of a Capillary Driven Blood Plasma Separation Microfluidic Device," Thesis [online], Universitat Politecnica de Catalunya, Nov. 2013 [retrieved on Mar. 27, 2018], Retrieved from the Internet: http://upcommons.upc.edu/handle/2117/96085, 99 pp.
Zulfigar, A., et al., "Fabrication of Polyimide Based Microfluidic Channels for Biosensor Devices," Journal of Micromechanics and Microengineering, Feb. 11, 2015, vol. 25, No. 3, 9 pp., DOI: 10.1088/0960-1317/25/3/035022.

\* cited by examiner

HARVESTING CELL-FREE NON-CODING RNAS (CFNCRS) FROM INTERSTITIAL FLUID FOR SENSITIVE BIOMARKERS

CROSS-REFERENCE TO RELATED APPLICATIONS

The present application claims the benefit of priority to similarly titled U.S. Provisional Patent Application Ser. No. 62/452,820 filed on Jan. 31, 2018 which is incorporated herein by reference in its entirety.

BACKGROUND

Field of the Embodiments

The present embodiments generally relate to the collection of bodily fluids for clinical testing and more particularly to devices and processes for the collection of interstitial fluid from an individual.

Description of Related Art

The discovery of cell-free non-protein-coding RNAs, or simply non-coding RNAs (cfNCRs), in the last decade has led to insights for their application as sensitive biomarkers for cancers and other human diseases. The importance of this emerging field of study has been explicitly recognized and just some of the potential applications identified as discussed in the Turchinovich et al. editorial, The origin, function and diagnostic potential of extracellular cfNCR in human body fluids, published in Frontiers in Genetics, February 14, Volume 5, Article 30. For example, one class of extensively studied cfNCRs is microRNAs (miRNAs), which have relatively short sequences of about 18 to 22 nucleotides. The traditional view of human physiology is that in general, proteins form the basis for signaling molecules in cellular communication. However, the discovery of their presence not only in tissues but also in human body fluids (plasma, serum, saliva, urine, cerebro-spinal fluid, tears, and milk) has implicated these functional cell-free (extracellular) circulating miRNAs as potentially informative biomarkers of disease. Furthermore, it suggests a more intricate level of cellular communication and regulation may exist, where secretion of circulating miRNAs into the body fluids allow them to be stably transported to other parts of the body thereby broadcasting their signal systemically. Eventually, they are taken up by the appropriate recipient cells. Of particular note is that circulating miRNAs can be detected in the serum and plasma of cancer patients, and are surprisingly stable despite the high amounts of enzymatic RNases circulating in the blood of cancer patients. Exploiting the diagnostic and prognostic potential of miRNAs as cancer biomarkers and other disease states relies mainly on their high stability. The molecular basis of this high stability is largely unknown, although possible mechanisms suggest that circulating miRNAs might have unique modifications (methylation, adenylation, and uridylation) that increases their stability and affords protection against RNases.

Studies in humans and complemented by animal models, demonstrate the importance of tissue cfNCRs, such as, miRNAs, during developmental processes and various disease pathologies. Thus, significant changes of tissue cfNCR "signatures" occur in various diseases, such as cancers, cardiovascular disease, diseases of the lung, kidney, and nervous system. However, routine biopsies from any one of these organs for cfNCR profiling is not practical. Therefore, it is apparent that a critical need exists for less invasive or noninvasive procedures for the detection of circulating cfNCR biomarkers.

Circulating cfNCRs are attractive candidates for disease monitoring to serve as valuable prognostic indicators of disease progression or even resolution. It has been predicted that changes in cfNCR expression in body fluids occur earlier than standard biomarkers. For example, troponin and C-reactive protein are typical markers of inflammation and repair in the cardiovascular and lung systems. However, by the time these proteins are detectable in the circulation, much of the tissue damage has already occurred, which makes it crucial that better biomarkers be uncovered for the early detection of diseases.

Secreted cfNCRs have many characteristic features that are essential for their use as practical biomarkers. As was noted, cfNCRs are stable in various bodily fluids, but they can be extracted and measured while the sequences are conserved. The concentration of cfNCRs can be detected using quantitative polymerase chain reaction (PCR), the gold standard for cfNCR quantification in clinically certified laboratories.

By way of particular, non-limiting example, alterations of miRNA levels in body fluids have already been associated with several diseases. The identification of cell-free miRNA in patients with diffuse large B cell lymphoma indicated that high levels of tumor-specific miR-21 correlated with improved relapse-free survival. Similar studies show several other circulating miRNA have been identified as potential biomarkers for cancer diagnosis and prognosis. Circulating miRNAs are also associated with inflammatory diseases. Levels of circulating miR-146a and miR-223 were significantly reduced in septic patients, when compared with healthy controls, while miR-150 levels in leukocytes and plasma correlate with the aggressiveness of sepsis. Reduced plasma levels of miR-132 were observed in patients with rheumatoid arthritis and osteoarthrosis compared with healthy controls. Furthermore, during acute myocardial infarction, plasma levels of the cardiac-specific miR-208 are shown to be elevated.

Despite the huge potential for circulating cfNCRs to act as biomarkers, much of the work currently focuses on either plasma or serum for their collection. The reason for this is simple—blood draws are ubiquitous and the simplest in a clinical setting. Other body fluids could be used however, standard protocols generally do not exist and the composition of these fluids is quite dissimilar, which implies that cfRNA isolation methods cannot be directly transposed from plasma/sera to another fluid. However, several major problems exist with cfNCRs obtained from blood including, among other things; the need for the introduction of interfering anticoagulants; the fact that platelet-derived cfNCRs are present in plasma and serum and thus, with some medical conditions, platelet counts increase and may be reflected as changes in plasma or serum cfNCR expression patterns; although extracellular cfNCR s are stable in purified plasma or serum, it is possible that the cellular components of blood are releasing cfNCRs during the storage period that would alter their initial concentration; cfNCR isolation from plasma and serum requires denaturing and removal of any sample protein content (albumin, immunoglobulins, coagulation components, etc.); and the need for cell lysis, which would increase the "noise" in samples. Some additional discussion on the suitability of obtaining cfNCR from blood samples can be found in Mielczarek, et al., Microfluidic blood plasma separation for medical diagnostics: is it worth it?, DOI: 10.1039/C6LC00833J (Frontier) Lab Chip, 2016, 16, 3441-3448 which is incorporated herein by reference and various articles cited therein.

For this technique to advance to the next stage, there is an obvious, critical, yet un-met need, to obtain extracellular cfNCR signatures from body fluids, other than blood, collected by non-invasive means.

Interestingly, one bodily fluid that is commonly disregarded or omitted from the list of testable bodily fluids is interstitial fluid (ISF), which also surrounds all living tissue and organs and contains constituents of the blood that are typically size excluded to being <60 kDa. Thus, clinical testing of ISF provides a completely new body fluid for diagnostic applications that has not seen any extensive use. This is mainly due to the collection methods currently available—the suction blister method described in J. Kool et al., "Suction blister fluid as a potential body fluid for biomarker proteins", *Proteomics*, 7(20), 3638, 2007 (hereafter "suction method") and the cantharide-induced skin blister method as discussed in M. Brunner, et al., "Direct assessment of peripheral pharmacokinetics in humans: comparison between cantharides blister fluid sampling, in vivo microdialysis and saliva sampling", *Br J Clin Pharmacol.*, 46(5), 425, 1998 (hereafter "blister method"), both interestingly considered as non-invasive.

Figure 1A:
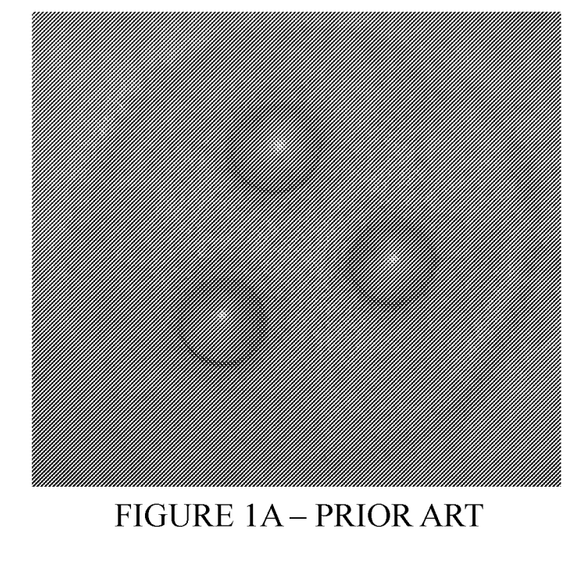
FIGS. 1A and 1B illustrate the results of prior art blister formation techniques used to collect ISF.
Figure 1B:
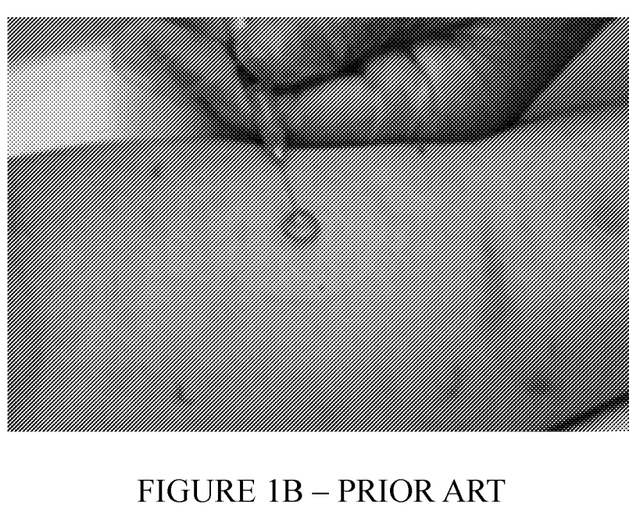

Referring to prior art FIGS. 1A and 1B, the suction method involves the application of vacuum suction on the skin surface for at least 2 hours, resulting in the epidermis slowly becoming detached from the underlying dermis. The resulting induced blister fills with interstitial fluid that can be collected by piercing the blister with a syringe needle to draw the ISF. A variant of using a suction pump is to raise suction blisters using syringes, which can take more than 2 hours to produce. Although these procedures are considered as being painless, at worst causing itching and discomfort, the resulting wounds typically heal in 7 to 10 days without forming any scars. However, some subjects can develop hyperpigmentation at the wound sites that can last for months or longer.

The blister method for obtaining ISF samples relies on the toxic reaction of cantharide on the skin to generate sub-epidermally located skin blisters. Cantharides are blistering agents made from the powdered, dried bodies of Lytta vesicatoria, or the blister beetle. The principle component of cantharide is cantharidin, the blistering agent shown to potentially cause adverse effects. For this reason, it has been included in a list of "problem drugs". However, when compounded properly and applied in the clinic topically by medical personnel familiar with its effects and uses, cantharidin can be safely and effectively used to treat some benign skin lesions like warts. In order to collect ISF, the cantharides are impregnated onto a dermal patch and adhered to the skin for 12 hours. The resulting blister fluid can be aspirated into a syringe by puncturing the blister with a fine needle, similar to the collection strategy used in the suction method.

An even more invasive approach to collect ISF is to use micro-needles to draw the ISF as described in the article by A. V. Romanyuk et al. entitled "Collection of Analytes from Microneedle Patches," Anal Chem. 2014 Nov. 4; 86(21): 10520-10523 ("Romanyuk et al.").

Obviously, the methods above used to harvest interstitial fluid are uncomfortable, time-consuming, and intrusive, and a blood draw would likely seem to provide a simpler course.

Accordingly, a less invasive and more efficient device and process for collecting ISF would be welcome by both patients and the clinical community.

SUMMARY OF EMBODIMENTS

A first exemplary embodiment includes a system for determining the presence of cell-free non-coding RNA (cfNCR) biomarkers in interstitial fluid. The system includes: a microfluidic sampling device for non-invasively and passively accessing interstitial fluid from a patient, the microfluidic sampling device further including at least one source of analysis fluid to be mixed with accessed interstitial fluid; and an analysis device for receiving an amount of the mixture analysis fluid and accessed interstitial fluid to determine the presence of one or more cfNCR biomarkers therein.

A second exemplary embodiment includes system for determining the presence of cell-free non-coding RNA (cfNCR) biomarkers in interstitial fluid. The system includes: a microfluidic sampling device for non-invasively and passively accessing interstitial fluid from a patient, the microfluidic sampling device further including at least one source of analysis fluid to be mixed with accessed interstitial fluid, the microfluidic sampling device including a first layer formed of Kapton; a second layer formed of poly(dimethylsiloxane) (PDMS), wherein the first and second layer are bonded together; an array of vertical microchannels formed through the first and second layer; and at least one electrically controllable microheater formed at a Kapton end of each of the vertical microchannels; and an analysis device for receiving an amount of the mixture analysis fluid and accessed interstitial fluid to determine the presence of one or more cfNCR biomarkers therein.

DETAILED DESCRIPTION

Figure 2A:
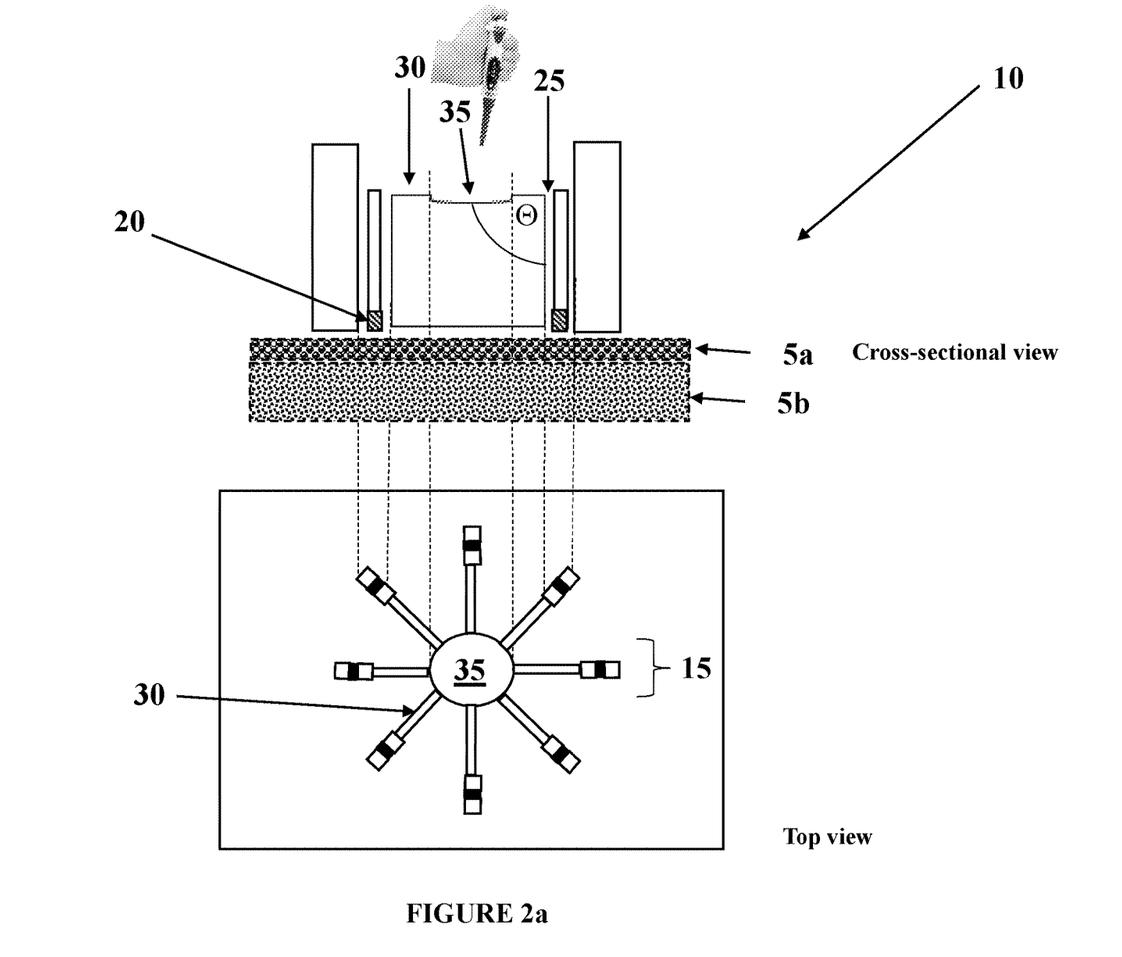
FIGS. 2a and 2b illustrate an exemplary embodiment of the present invention wherein a microheater and microchannel configuration with a collection reservoir which may be used to collect ISF.
Figure 2B:
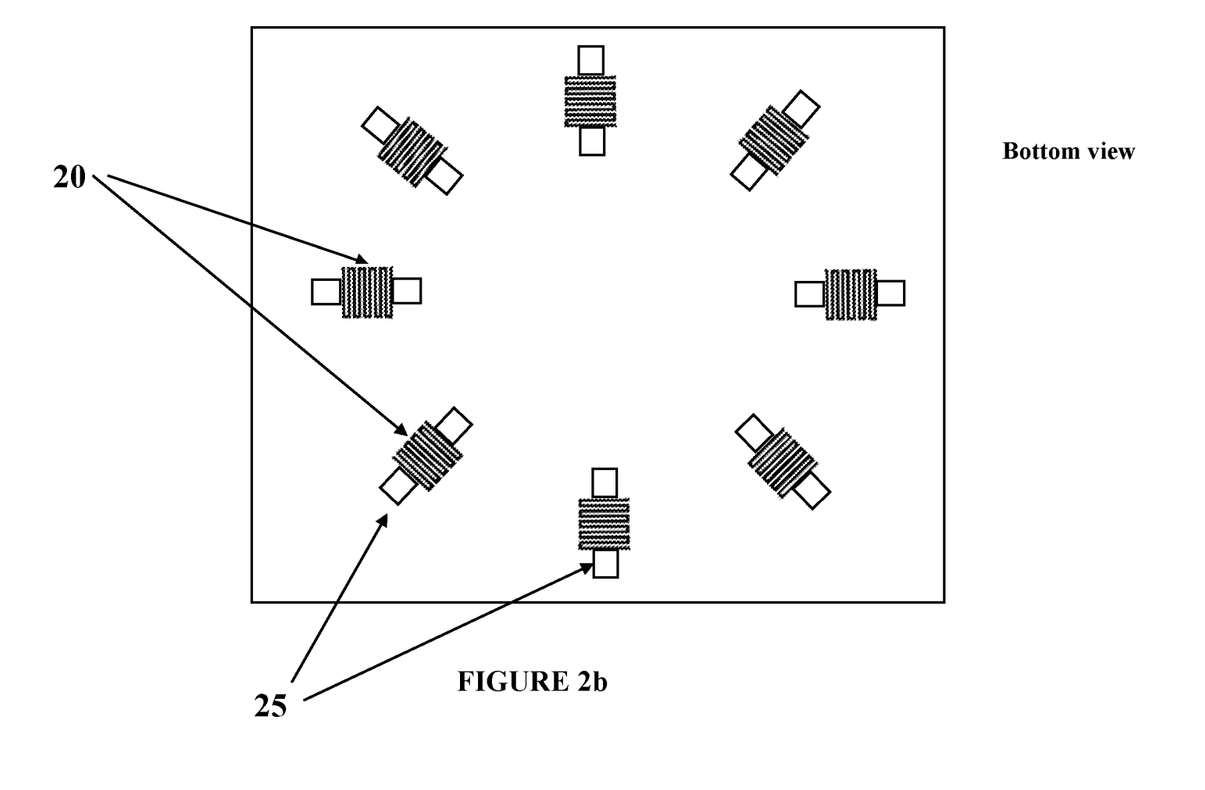
Figure 3:
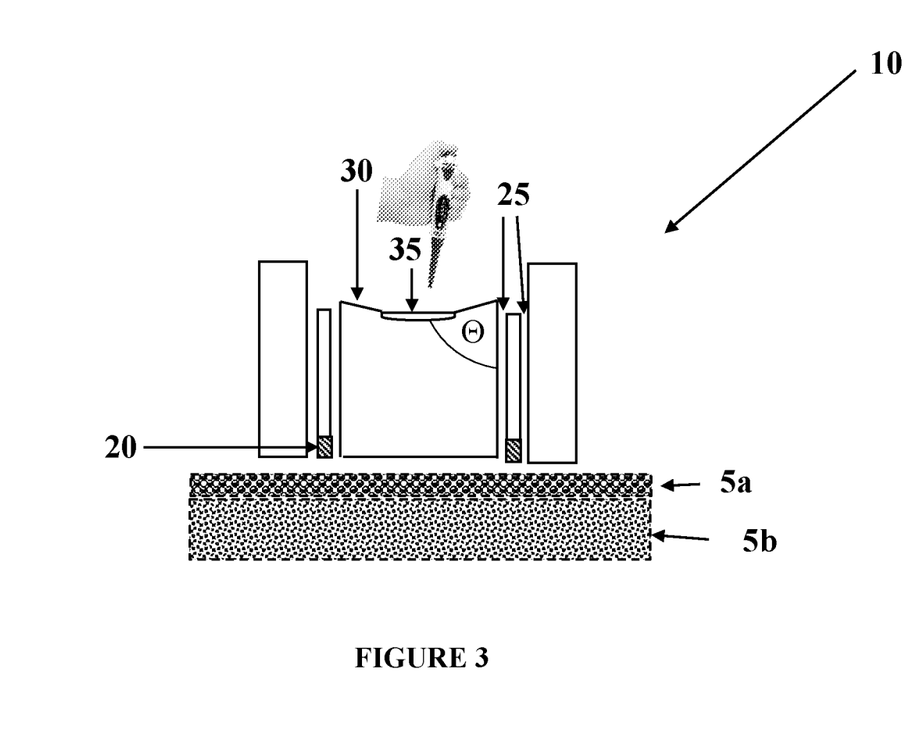
FIG. 3 illustrates a first exemplary embodiment of the present invention wherein a microheater and microchannel configuration with a collection reservoir may be used to collect ISF.

The present embodiments outline a simple, effective, and time efficient way to painlessly collect ISF from a patient and assess the presence of cfNCR biomarkers in the ISF using standard clinical methods (e.g., mass spectrometry, liquid chromatography, etc.). The devices described herein utilize microfluidic technology to help in the transfer process of ISF from the skin surface to a collection port for subsequent aspiration by pipetting (see FIG. 2a). The ISF originates using, for example, thermal ablation micro-heaters 20, situated on the device surface, or inset therein that will be placed in contact with the top layer of the skin containing dry, dead skin cells, or stratum corneum, 5a. Multiple micro-heaters 20 may be activated simultaneously or in succession in order to harvest larger volumes of ISF, as needed, from lower layers of skin 5b. FIGS. 2a and 2b illustrate cross-sectional, top and bottom views of an exemplary system 10 having 8 individual ablation/collection sites 15. At each collection site 15, there is a single microheater 20 flanked by two vertical micro-channels 30. The micro-heaters and channels may be in various shapes and configurations, including rectangular, square, circular or combinations thereof. The dimensions of the vertical microchannels may be on the order of approximately 50-100 microns per side. The spatial separation distance between sites 15 can be determined, and varied, based on whether dermal trauma is indicated. The ISF resulting from the thermal ablation is transported through hydrophilic vertical micro-channels 25 by capillary action, and connected to approximately horizontal micro-channels 30 oriented substantially in the plane of the device surface and ending at a common collection port 35. Each vertical micro-channel 25 with a corresponding substantially horizontal micro-channel 30 is formed in the substrate with angle θ therebetween. These generally planar micro-channels can be arranged in any way that maximizes collection, such as with a spoke-like configuration illustrated in FIG. 2a. In FIG. 3, the approximately horizontal microchannels are oriented so as to be slightly inclined towards the central collection port 35 such that angle θ is less than 90 degrees. In both configurations, the collection port 35 may be indented slightly to pool the ISF from the horizontal channels 30, although such an indentation is not required.

Figure 4A:
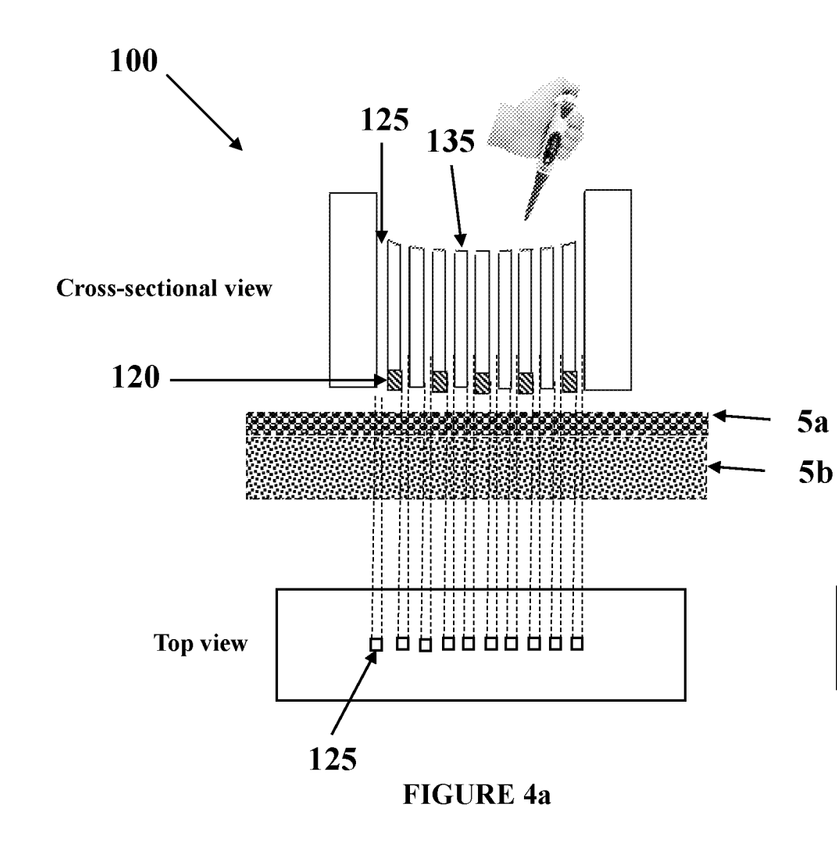
FIGS. 4a to 4c illustrate a second exemplary embodiment of the present invention wherein a microheater and microchannel configuration with a collection reservoir may be used to collected ISF.
Figure 4B:
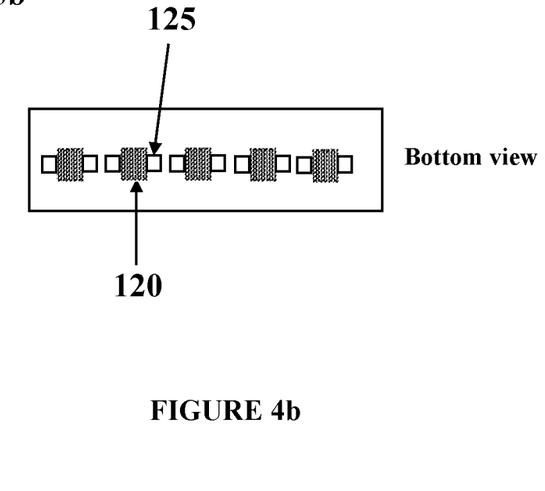
Figure 4C:
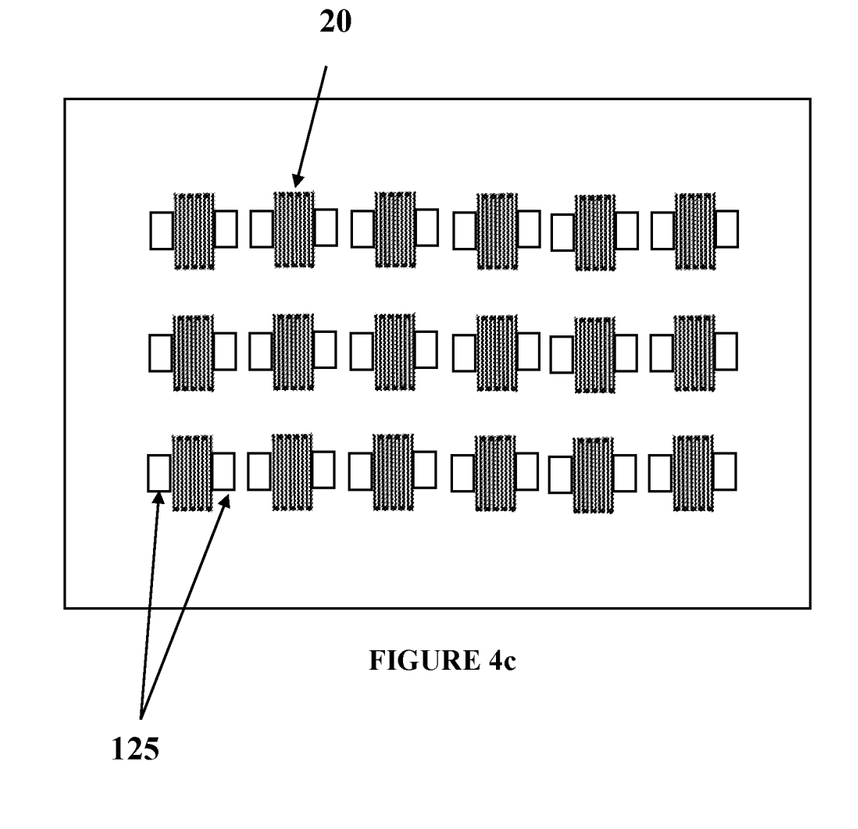
Figure 5A:
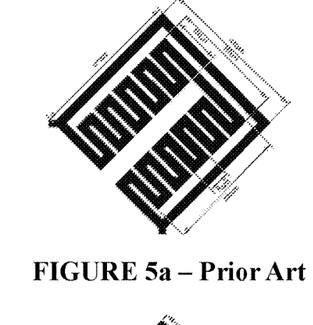
FIGS. 5a to 5i illustrate exemplary prior art micro-heater configurations for use with one or more of the exemplary embodiments described herein.
Figure 5B:
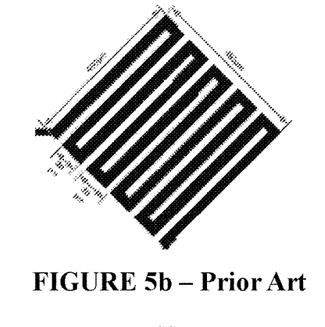
Figure 5C:
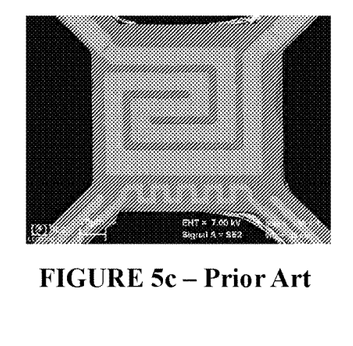
Figure 5D:
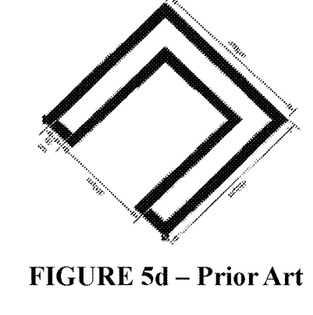
Figure 5E:
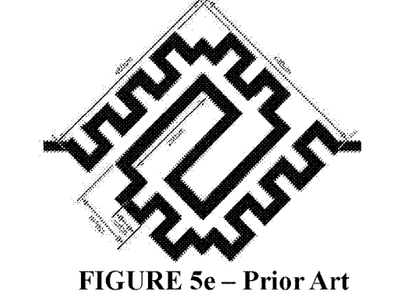
Figure 5F:
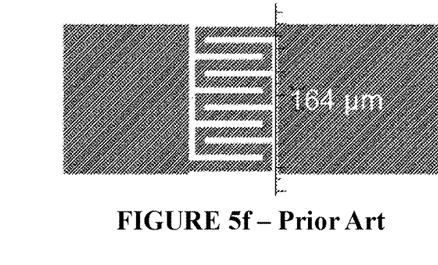
Figure 5G:
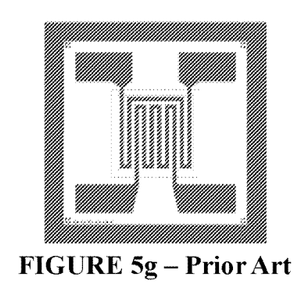
Figure 5H:
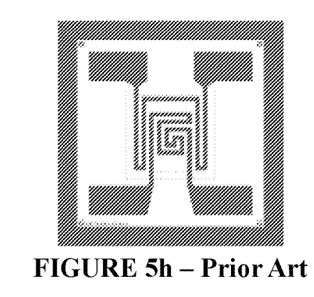
Figure 5I:
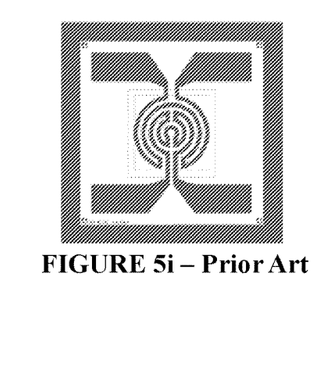

Alternatively, FIGS. 4a-4c illustrate a system 100 having different collection geometries wherein multiple vertical micro-channels 125 simply terminate at a central collection area 135 and the ISF can be extracted from the central collection area 135 for analysis. The number of collection channels feeding the central collection area and the arrangement thereof is not limited. FIGS. 4a and 4b show a configuration having a line of 10 separate collection channels 125 whereas FIG. 4c shows a bottom view of a 12×3 array of collection channels 125. In FIG. 4a, the collection area 135 is shown as being formed so as to resemble a trough or bowl to better collect the ISF for extraction. This trough or bowl configuration of the central collection area 135 is not required.

The thermal ablation micro-heaters 120 function to ablate a microscopic portion of the stratum corneum containing dry, dead skin cells, the topmost layer of skin 5a, so that the interstitium, part of lower layer 5b, can be exposed, releasing ISF. The micro-heaters 120 are in close proximity to the skin surface, together with electrical components that control current to the micro-heaters 120. Each micro-heater preferably comprises a pair of electrodes connected by a conductive pathway that is arranged, either by the use of a resistive material or by a serpentine conductive pathway, to provide sufficient resistance to the flow of electricity such that an effective amount of heat is produced so as to locally ablate an appropriate portion of the stratum corneum. Electrical connections may also be provided to each of the two electrodes to connect the micro-heating unit to a controller that controls the application of an electrical current source to the electrodes, thus providing for individualized control of heating on a per micro-heater 120, per collection site 15 basis. In operation, the micro-heater 120 is pulsed with a suitable alternating or direct current to provide local ablation. Control of the duration and intensity of the heating pulse is preferably carried out to effect ablation of the desired area and depth. The micro-ablation preferably occurs in a confined volume of the stratum corneum. By way of example only, an area having the dimensions of approximately 50 μm×50 μm×40 μm may be suitable for collection of an adequate amount of ISF. Alternative embodiments are contemplated wherein the individual micro-heaters may be for single-use, as compared to multiple use, such that when the individual micro-heater is used, the heating circuit is "blown" and may not be used again.

Additional details regarding micro-heater configurations and details which may be used with one or more of the embodiments herein may be found in commonly owned and similarly titled U.S. Pat. Nos. 6,887,202, 7,931,592, 8,568,315 and 9,332,937, which are incorporated herein by reference.

Figure 6:
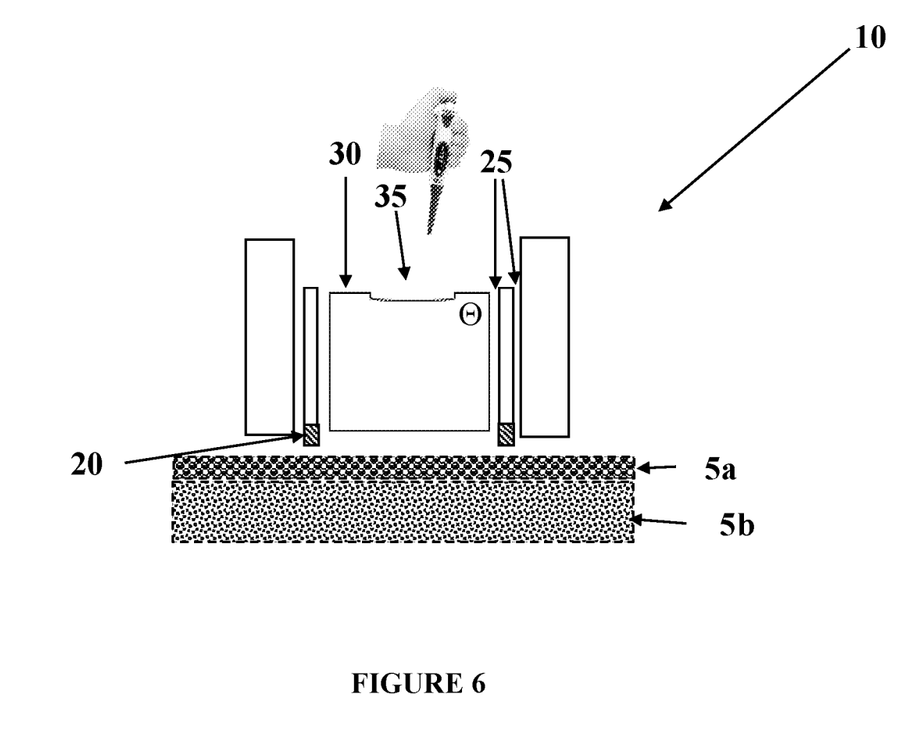
FIG. 6 illustrates an alternative micro-heater placement configuration within one or more of the exemplary embodiments described herein.

Exemplary prior art micro-heater configurations are shown in FIGS. 5a-5i. Although rectangular, serpentine micro-heaters are shown in the figures, the embodiments are not so limited. Further, variations to the placement of the micro-heaters with respect to the opening of the vertical microchannels is not limited to the configuration shown in the figures. That is, alternative configurations contemplate that instead of being inset within the substrate, some portion of the micro-heater may be layered on the substrate and thus be protruding therefrom as shown in FIG. 6. Further, it is contemplated that the suspension may be achieved from a single side of the opening. Fabrication techniques and materials for suspending the heater across the opening of each vertical micro-channel are known to those skilled in the art. The following articles discuss suspended microheaters and the substance thereof is incorporated herein by reference: Hotovy et al., Gallium arsenide suspended microheater for MEMS sensor arrays, Microsyst Technol (2008) 14:629-635; Sidek et al., Effect of Heater Geometry on the High Temperature Distribution on a MEMS Micro-hotplate, $3^{rd}$ Asia Symposium on Quality Electronic Design, IEEE 2011; Chau et al., Design and fabrication of a quasi-ordered nanoporous silicon membrane suitable for thermally induced drug release, J. Micromech. Microeng. 22 (2012) 085028 (14 pp).

Figure 7:
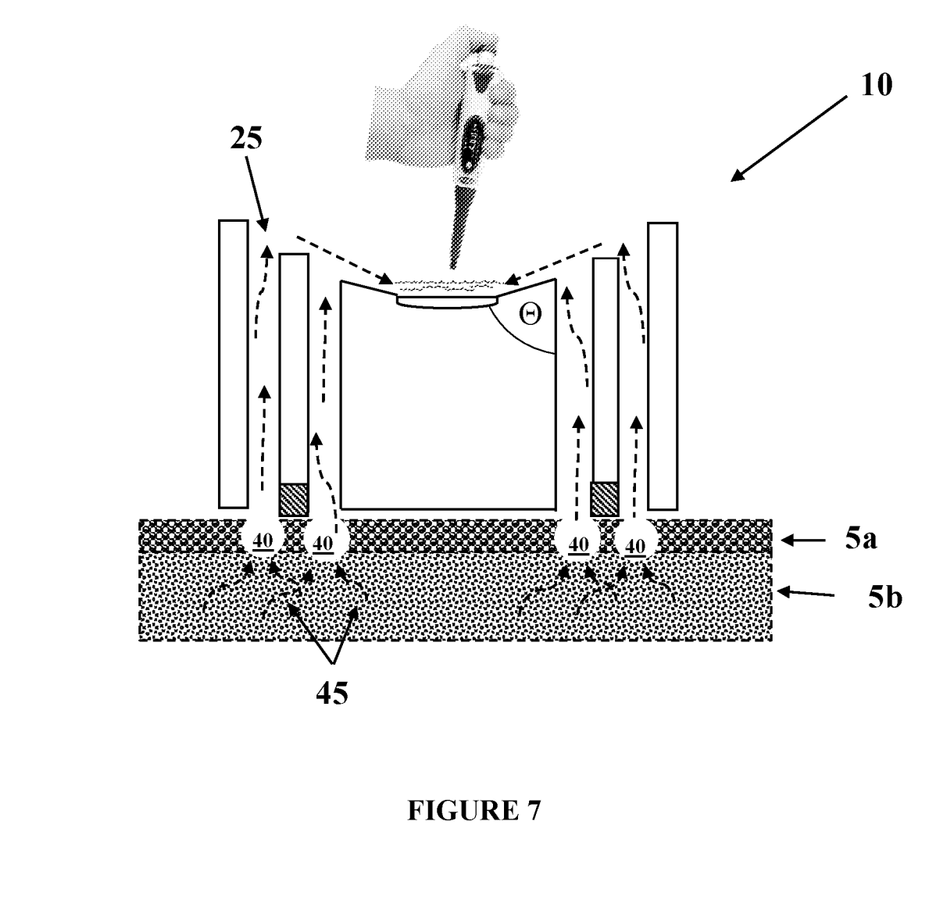
FIG. 7 illustrates the embodiment of FIGS. 2a and 2b during use.

Using the embodiment from FIGS. 2a-2b as an example, FIG. 7 illustrates the configuration after the stratum corneum 5a has been ablated by micro-heaters 20 to form micropores 40 therein and access the ISF 45, which is shown by broken arrows. The ISF is drawn up through the vertical micro-channels 25 by capillary action.

For ease of fabrication and processing, the representative structure may be formed in poly(dimethylsiloxane) (PDMS) or KAPTON® (polyimide), but it is understood by one skilled in the art that this is not the only material that can be used. PDMS channels may be formed using a molding process with high aspect ratio photoresist (SU-8) while Kapton can be chemically etched using patterned protective layers of metallic films. Laser processing may also be used for both PDMS and KAPTON®. In an alternative embodiment, the final device may be comprised of PDMS bonded with KAPTON®, where KAPTON® is the layer containing the microheaters and in contact with the skin, while the PDMS serves to transport the ISF upwards. Since PDMS is inherently hydrophobic, it is treated to render it hydrophilic. This may be accomplished by adding a nonionic organosilicone surfactant such as SILWET®.

Figure 8:
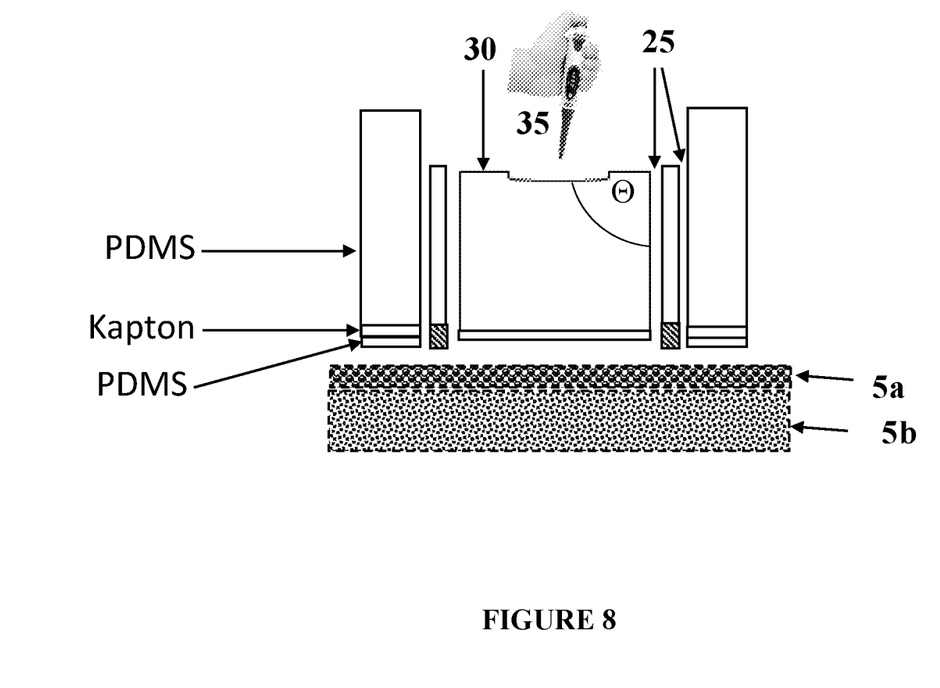
FIG. 8 illustrates an alternative embodiment of the device using combinations of materials.

Alternatively, as shown in FIG. 8 an additional thin PDMS layer with openings for the microheater and microchannels can be added to the KAPTON® layer to provide a hydrophobic surface to aid in guiding ISF to the vertical microchannels from the skin. The result is that the microheaters 20 are very slightly recessed from the main surface of the device as shown, but are still well within heating reach of the skin. The thin PDMS layer may be on the order of 100 microns thick.

Figure 9A:
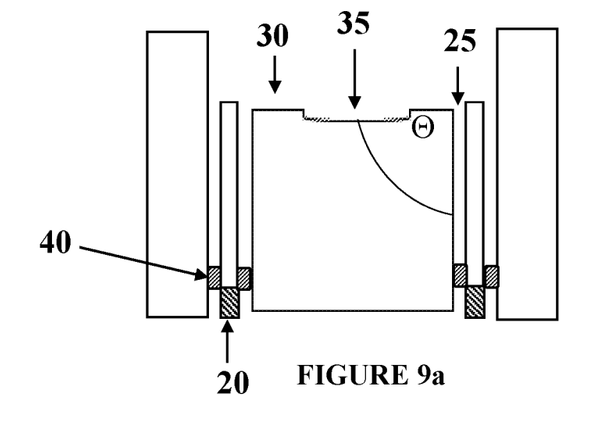
FIGS. 9a-9c illustrate exemplary embodiments wherein reservoirs containing analysis fluid are included within the microfluidic devices.
Figure 9B:
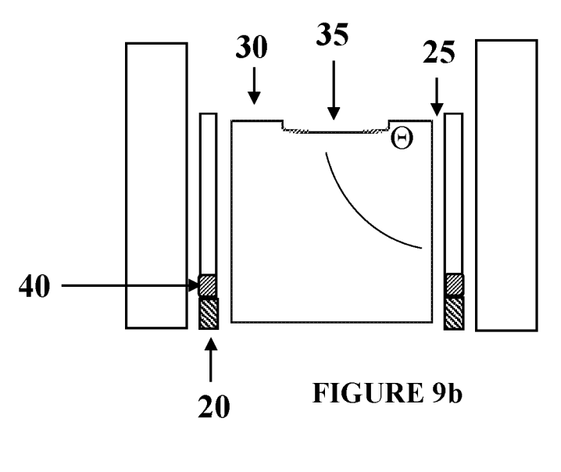
Figure 9C:
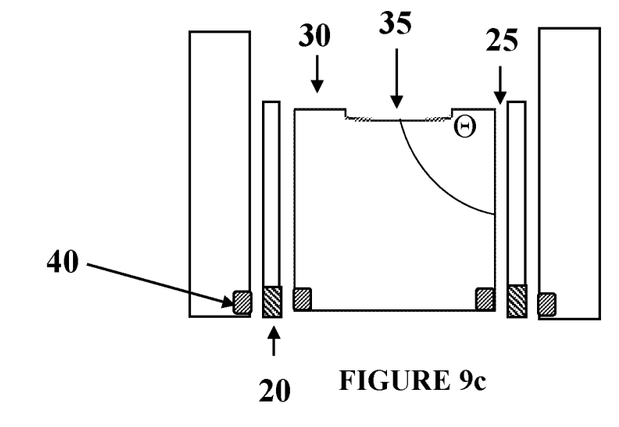

Another possible technique to assist in the analysis of the harvested ISF employs mixing of the ISF with one or more analysis fluids during collection of the ISF via the microfluidic channels. Referring to exemplary devices shown in FIGS. 9a-9c, such analysis fluids may be located in, for example, one or more initially sealed reservoirs 40 which has been manufactured in (FIG. 9a) to or adjacent to (FIGS. 9b, 9c) each (or some subset) of the vertical microchannels and in close enough proximity to the individual microheaters at each of the individual collection sites to rupture the seal to the reservoir and release the analysis fluid into the micro-channel at approximately the same time that the microheater is disrupting the stratum corneum to access the ISF.

Figure 10:
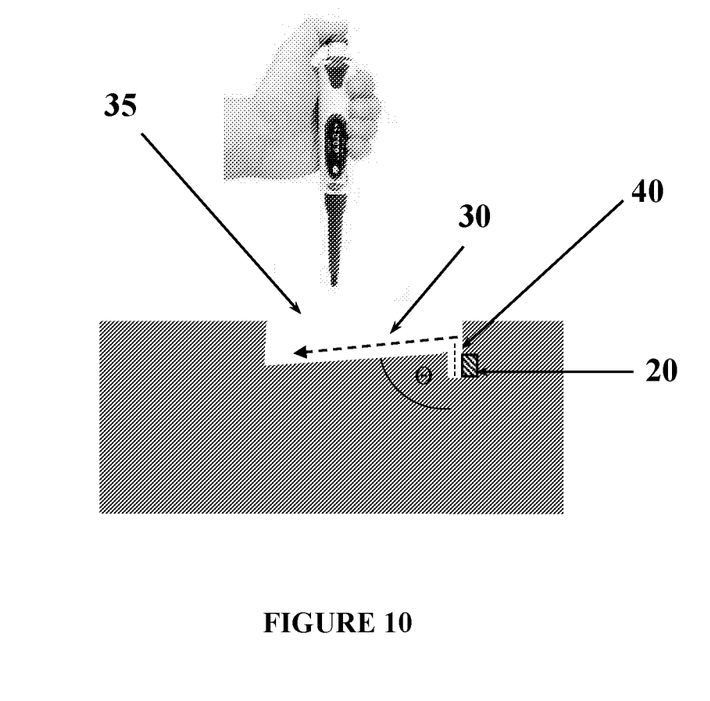
FIG. 10 illustrates an alternative exemplary embodiment wherein reservoirs containing analysis fluid are included within the microfluidic devices.

Alternatively, some number of the individual collection sites, e.g., 1 up to 7 in the 8-site example shown in the spoke configuration, could be dedicated solely to one or more reservoirs 40 containing analysis fluid(s). For example, every other site could be a reservoir, while the alternating sites contain the vertical microchannels and microheaters for accessing the ISF, see for example, FIG. 10, which is a cross-section view of a reservoir site as part of a larger collection system in the 8 spoke configuration of FIG. 2a, 2b. The reservoir 40 is located at the end of the spoke where the vertical microchannel begins for the ISF collection sites. The reservoir 40 may be sealed, in which case a microheater may also be located in proximity thereto to break the seal.

To facilitate mixing of the ISF with the analysis fluid, the entire microfluidic device may be placed in a controllable mixing device to mix the analysis fluid with the accessed interstitial fluid from the patient prior to accessing from the collection area. One skilled in the art will recognize that a suitable device may be a controllable centrifugal device for controllably spinning the microfluidic sampling device.

The systems described herein are novel liquid biopsy systems which use a less invasive and alternative approach to, e.g., the standard cancer tissue biopsy for obtaining genetic and epigenetic anomalies that contribute to oncogenesis and cancer progression. The systems allow the liquid sampling to be truly non-invasive and have significant sample processing advantages when compared with blood. Especially relevant in the liquid biopsy technique is the need for serial sample collection to monitor disease progression or response to a treatment. Currently, blood is the clinically-preferred sample matrix, and much work has been undertaken to investigate ways to make sample processing easier and reliable. But to date, no research has been conducted on using ISF as a new sample matrix, wherein the human capillary system has inherently performed a pre-filtration of every biomolecule that is >60 kDa. The ISF collected using the transdermal systems described herein contain no red or white blood cells, platelets, or large plasma proteins. The ISF does contain is a host of low molecular mass biomarkers including glucose, lactate, and a variety of circulating cell-free DNA (cfDNA) and non-coding circulating RNA species.

Much research has already been devoted to cfDNA for cancer patients, where mutated DNA derived from dying or lysed cancer cells can be isolated, sequenced and analyzed for abundance as an indicator of a patient's tumor burden. Using serial monitoring, changes in mutation pattern over time can indicate altered pathways or clonal evolution of the disease, while an altered abundance of mutated DNA suggests an altered disease burden. Additionally, during the course of treatment, changes in circulating DNA mutation patterns can indicate the emergence of resistant clones and could prompt a change in treatment. In contrast to mutant DNA, cell-free non-coding RNAs are transcribed, processed, packaged and released from cells in both normal and diseased tissue as part of the extracellular communication between cells. As a result, cfNCR expression patterns can be used to establish a person's baseline steady-state condition while serial samples can monitor alterations over time, indicative of an altered physiologic or disease state, or changes in response to therapeutic intervention. Thus, by using non-invasively obtained ISF, serial analysis of mutant DNA combined with the companion diagnostic cfNCR analysis provides a highly specific molecular signature of a disease state and can be used to monitor treatment responses or resistance to treatment in real time with a minimally invasive and less arduous procedure.

Further, the accessing and analysis systems and techniques described above are not limited to determination of miRNA. The recent discovery of a significant number of other cell-free small non-coding RNA (cfNCR) species provides an additional pool of potential host biomarkers including but not limited to: additional extracellular circular RNAs (cirRNAs) whose biogenesis are formed by back-splicing events in higher eukaryotic cells and are extremely stable in clinical body fluids and piwi-interacting RNAs (piRNAs) which are small (26-31nt) non-coding cell-free RNA molecules expressed in animal cells that form RNA-protein complexes. Further, the ability to determine existence of and analyze certain cell-free small non-coding RNA may signal extracellular mutations, immune cell presence and activity and other biomarker information. Such information could be useful and critical to providing warnings regarding malignancy, infectious pathogen exposure/disease, immune suppression issues and a whole range of other signals.

By way of specific example, miRNAs are hypothesized to act as signaling molecules via binding to intracellular Toll-like receptors (TLRs); characteristic of immune cells involved in the innate immune system. Further still, studies have indicated that piRNAs were surprisingly abundant in cerebrospinal fluid (CSF) when compared with other body fluid or intracellular samples; such cfNCRs may also be found in ISF. It is further contemplated that "liquid biopsy" targeting of extracellular sequence mutations as cancer genotyping biomarkers for several somatic mutations derived from malignant tumors may be achieved by tracking, for example, information from cfNCR derived from bodily fluids, e.g., ISF. Additionally, pathogen small RNAs colonizing strains have been discriminated in saliva from strains in patients with bloodstream infections, including patients with sepsis and septic shock using pathogens small RNAs; it is hypothezied that similar strains may be found in other bodily fluids, such as ISF. The present invention offers an alternative to blood draw and other invasive techniques for ascertaining cfNCR rich ISF.

The following patents and patent applications, which are co-owned by the Applicant and include an overlapping inventor with the present application, are incorporated herein by reference in their entireties and variations to the present embodiments in accordance with one or more teachings therein are considered to be within the scope of these embodiments: U.S. Pat. No. 6,887,202, titled "Systems and Methods For Monitoring Health and Delivering Drugs Transdermally," U.S. Pat. No. 7,931,592, titled "Systems and Methods For Monitoring Health and Delivering Drugs Transdermally," U.S. Pat. No. 8,568,315, titled "Systems and Methods For Monitoring Health and Delivering Drugs Transdermally," U.S. Pat. No. 9,332,937, titled "Systems and Methods For Monitoring Health and Delivering Drugs Transdermally," US Pub. No. 2013-0289374, titled "Electrochemical Transdermal Glucose Measurement System Including Microheaters and Process For Forming," U.S. application Ser. No. 13/835,696, titled "Microfluidic Systems For Electrochemical Transdermal Glucose Sensing Using a Paper-Based or Other Wicking Substrate," U.S. application Ser. No. 13/834,199, titled "Microfluidic Systems For Electrochemical Transdermal Analyte Sensing Using a Capillary-Located Electrode," and U.S. application Ser. No. 15/226,475, titled "Apparatus and Method For Delivery of Antimicrobial During a Transdermal Sampling and Delivery Process."

The invention claimed is:

1. A system for determining the presence of cell-free non-coding RNA (cfNCR) biomarkers in interstitial fluid comprising:
   a microfluidic sampling device for non-invasively and passively accessing interstitial fluid from a patient, the microfluidic sampling device further including at least one source of analysis fluid to be mixed with accessed interstitial fluid, wherein the microfluidic sampling device includes
      a substrate containing multiple vertical micro channels therethrough, wherein at a first end of each of the multiple vertical micro channels a microheater is formed for controllably ablating a portion of skin to access the interstitial fluid; and
      further wherein at a second end of each of the multiple vertical micro channels is a horizontal micro channel for receiving accessed interstitial fluid from a vertical micro channeland guiding the accessed interstitial fluid to a common collection port; and
   an analysis device for receiving an amount of the mixture of analysis fluid and accessed interstitial fluid to determine the presence of one or more cfNCR biomarkers therein.

2. The system according to claim 1, wherein a reservoir containing the analysis fluid is formed in or in contact with one or more of the vertical micro channels and the microheater therein and the microheater operates to rupture a seal of the reservoir and release the analysis fluid into the vertical micro channel.

3. The system according to claim 1, wherein an angle between each of the multiple vertical micro channels and a corresponding horizontal micro channel is less than 90 degrees.

4. The system according to claim 1, wherein the analysis device is selected from achromatography device and a PCR device.

5. The system of claim 1, wherein the microfluidic sampling device is formed in poly(dimethylsiloxane) (PDMS) or polyimide.

6. The system of claim 1, wherein the microfluidic sampling device is formed of bothpoly(dimethylsiloxane) (PDMS) and polyimide.

7. The system of claim 1, wherein a first end of each of the multiple vertical micro channels containing the microheaters is formed of polyimide and a second end of each of the multiple vertical micro channels, the horizontal micro channels and the common collection port are formed of PDMS.

8. The system of claim 7, wherein the PDMS is treated to make it hydrophilic.

9. The system of claim 8, wherein the PDMS is treated by adding a nonionic organosilicone surfactant.

10. The system of claim 1, wherein the multiple vertical micro channels, multiple horizontal micro channels and the common collection port are arranged in a spoke and wheel configuration, wherein the multiple horizontal micro channels end at the common collection port.

11. The system of claim 1, wherein the microheaters are formed in-line with the first end of each of the multiple vertical micro channels at a circumference of an opening at the first end of each of the multiple vertical micro channels.

12. The system of claim 1, wherein the microheaters are formed in-line with the first end of each of the multiple vertical micro channels and at least a portion thereof is suspended across an opening at the first end of each of the multiple vertical micro channels.

13. The microfluidic device of claim 1, wherein the microheaters are formed so as to protrude from the first end of each of the multiple vertical micro channels at a circumference of an opening at the first end of each of the multiple vertical micro channels.

14. A system for determining the presence of cell-free non-coding RNA (cfNCR) biomarkers in interstitial fluid comprising:
   microfluidic sampling device for non-invasively and passively accessing interstitial fluid from a patient, the microfluidic sampling device further including at least one source of analysis fluid to be mixed with accessed interstitial fluid, the microfluidic sampling device including
      a first layer formed of polyimide;
      a second layer formed of poly(dimethylsiloxane) (PDMS), wherein the first and second layer are bonded together;
      an array of vertical micro channels formed through the first and second layer; and at least one electrically controllable microheater formed at a polyimide end of each of the vertical micro channels, wherein a PDMS end of each vertical micro channel is fluidically connected to an approximately horizontal micro channel for directing interstitial fluid to a common collection port; and
   an analysis device for receiving an amount of the mixture analysis fluid and accessed interstitial fluid to determine the presence of one or more cfNCR biomarkers therein.

15. The system of claim 14, wherein the PDMS is treated to make it hydrophilic.

16. The system of claim 15, wherein the PDMS is treated by adding a nonionic organosilicone surfactant thereto.

17. The system of claim 14, the microfluidic sampling device further including a third layer formed of PDMS over a portion of the polyimide layer, but excluding each of the at least one electrically controllable microheater and each of the vertical micro channels.

18. The system of claim 14, wherein at least a portion of the electrically controllable microheaters is suspended across an opening at the polyimide end of each of the vertical micro channels.

19. The system of claim 14, wherein the microheaters are formed so as to protrude from the polyimide end of each of the vertical micro channels at a circumference of an opening at the polyimide end of each of the vertical micro channels.

* * * * *